United States Patent
Yan et al.

(10) Patent No.: US 9,580,462 B2
(45) Date of Patent: Feb. 28, 2017

(54) PROTEIN EXTRACTION METHODS

(75) Inventors: Lin Yan, Eden Prairie, MN (US); Quanzhi Li, New Brighton, MN (US)

(73) Assignee: Invent Biotechnologies, Inc., Eden Prairie, MN (US)

( * ) Notice: Subject to any disclaimer, the term of this patent is extended or adjusted under 35 U.S.C. 154(b) by 862 days.

(21) Appl. No.: 13/223,737

(22) Filed: Sep. 1, 2011

(65) Prior Publication Data

US 2012/0053328 A1 Mar. 1, 2012

Related U.S. Application Data

(60) Provisional application No. 61/378,999, filed on Sep. 1, 2010.

(51) Int. Cl.
*C07K 1/34* (2006.01)
*C12N 1/06* (2006.01)
*C07K 1/00* (2006.01)

(52) U.S. Cl.
CPC ..................... *C07K 1/34* (2013.01)

(58) Field of Classification Search
USPC ......... 435/320.1, 325; 530/387.1; 536/23.53; 424/178.1; 436/86; 514/19.3
See application file for complete search history.

(56) References Cited

U.S. PATENT DOCUMENTS 6,221,655 B1  4/2001  Fung et al.
6,242,220 B1  6/2001  Wahle et al.

OTHER PUBLICATIONS

Generon Ltd.*
"Antibody Pair Buffer Kit" datasheet [online]. Catalog No. CNB0011. Invitrogen, Camarillo, CA, Apr. 2010, [retrieved on Apr. 17, 2012]. Retrieved from the internet:<URLhttp://tools.invitrogen.com/content/sfs/manuals/CNB0011_Rev0410.pdf>; 1 pg.
"CytoSet™ Buffer Set" Technical Data Sheet, [online]. Catalog No. CNB0011. Invitrogen, Camarillo, CA, Sep. 2008, [retrieved on Jun. 8, 2010]; 1 pg. No longer available online. See Antibody Pair Buffer Kit above.
"Denaturing Cell Extraction Buffer Product Analysis Sheet" datasheet [online]. Catalog No. FNN0091. Invitrogen, Camarillo, CA, Sep. 2008, [retrieved on Jun. 8, 2010]. Retrieved from the Internet:<URL:http://tools.invitrogen.com/content/sfs/manuals/FNN0091_Rev%200908.pdf>; 1 pg.
"NE-PER® Nuclear and Cytoplasmic Extraction Reagents" datasheet [online]. Thermo Fischer Scientific Inc./Pierce Biotechnology, Rockford, IL, 2008, 4 pgs. This version no longer available online. See 2011 version listed below.
"NE-PER® Nuclear and Cytoplasmic Extraction Reagents" datasheet [online]. Thermo Fischer Scientific Inc./Pierce Biotechnology, Rockford, IL, 2011 [retrieved on Apr. 17, 2012]. Retrieved from the internet:<URL:http://www.piercenet.com/instructions/2160872.pdf>; 4 pgs.
"Protein Extraction Kit" datasheet [online]. Catalog #: EXT020, Full Moon Biosystems, Inc., Sunnyvale, CA. [Retrieved on Jun. 8, 2010]. Retrieved from the internet:<URL:http://www.fullmoonbiosystems.com/protocols/ProteinExtractionKit.pdf>; 3pgs.
"Protein Extraction Kits" datasheet [online]. EMD Millipore, Billerica, MA, © 1994-2010 [retrieved on Jun. 8, 2010]. Retrieved from the internet:<URL: http://www.millipore.com/immunodetection/id3/proteinextractionkits>; 5 pgs.
"Tissue Extraction Reagent I Product Analysis Sheet" datasheet [online]. Catalog No. FNN0071. Invitrogen, Camarillo, CA, Sep. 2008, [retrieved on Jun. 8, 2010]. Retrieved from the internet:<URL: http://tools.invitrogen.com/content/sfs/manuals/FNN0071_Rev%200908.pdf>; 1pg.
"Whole Cell Extraction Kit" datasheet [online]. Catalog No. 2910. Chemicon International/EMD Millipore, Billerica, MA, Dec. 2003 [retrieved on Jun. 8, 2010]. Retrieved from the internet;<URL:http://www.millipore.com/publications.nsf/a73664f9f981af8c852569b9005b4eee/a85f1796f57981c78525730600755389/$FILE/2910.pdf>; 4 pgs.

* cited by examiner

*Primary Examiner* — Kagnew H Gebreyesus
(74) *Attorney, Agent, or Firm* — Mueting, Raasch & Gebhardt, P.A.

(57) ABSTRACT

The present invention relates to methods for isolating polypepitdes from cells. The methods may be used to isolate denatured polypeptides or native polypeptides. In one embodiment the methods may be used to isolated polypeptide from cytosolic and nuclear compartments of eukaryotic cells. In one embodiment the methods may be used to isolate polypeptides from bacterial cells.

15 Claims, 6 Drawing Sheets

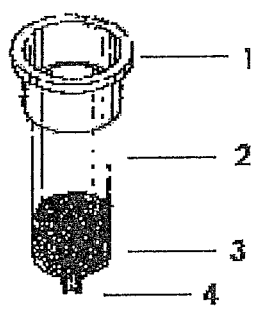
Figure 1
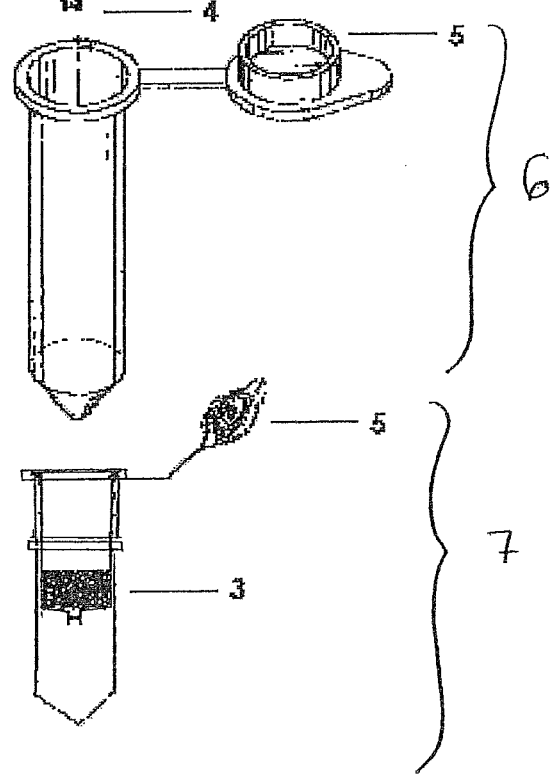
Figure 2
Figure 3
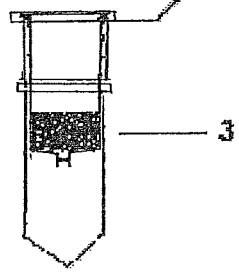

PROTEIN EXTRACTION METHODS

RELATED APPLICATIONS

This application claims the benefit of U.S. Provisional Application No. 61/378,999 filed Sep. 1, 2010, which is incorporated by reference in its entirety.

BACKGROUND

Extraction of proteins from total cell lysate is one of the most commonly employed procedures in biomedical research. The first step is to release proteins from the cells by chemical or physical methods. Cell lysis solutions containing denaturing detergents such as SDS, and non-denaturing detergents such as NP-40 and Tween-100 are frequently used in commercial kits for protein extraction (see, for instance, Pierce Protein Research Products, Thermo Fisher Scientific, Rockford, Ill., and PromoKine, Heidelberg, Germany). Though strong detergents such as SDS can lyse the cells efficiently, it also results in a very viscous solution due to the presence of released genomic DNA in the cell lysate, which is difficult to pipette and might interfere with subsequent protein quantification, gel electrophoresis and other downstream applications One of the most widely used laboratory methods to isolate proteins from total cell lysate is to extract proteins using detergent-containing solutions to lyse the cells followed by physical methods such as repeated sonication or passing the cell lysate through a fine needle repeatedly to shear DNA into smaller fragments and reduce the viscosity of the solution; however, these procedures are tedious and time consuming. Repeated sonication also generates significant heat that may inactivate the biological activities of proteins. Affinity purification of desired protein components using spin column filter assembly has been disclosed in U.S. Pat. No. 6,221,655 B1. A variety of commercial manufacturers have adopted the concept and are selling variations of spin column filters either as a stand alone unit or as a component of an assay kit for affinity purification of DNA and RNA (see, for instance, PureLink™ RNA Mini Kit).

SUMMARY OF THE INVENTION

This invention relates to methods for facilitating isolation and subsequent analysis of proteins from cell lysates through the use of protein extraction filter cartridges. The protein extraction filter cartridge may include a hydrophobic porous material (thickness >0.1 mm) with an average pore size of 30 µm (ranging from 20-60 µm) and a molded cylinder to hold the filter in place. Upon application of positive (such as centrifugation) or negative force (such as vacuum suction), proteins in the sample are rapidly separated from genomic DNA and cell/tissue debris. In one embodiment of this invention the cell is lysed with a buffer to release proteins, DNA, RNA, lipids and other cell components into a solution in the form of total cell lysate. The viscous cell lysate is transferred to protein extraction filter cartridge(s) indicated in the drawings (FIG. 1-3) which is subject to 30 seconds centrifugation in a microcentrifuge. The non-viscous protein extract is ready for subsequent analysis and downstream applications. Proteins isolated using the methods described herein may be in native or denatured forms which are suitable for applications such as protein electrophoresis, immunoblotting, ELISA, gel retardation, immunoprecipitation and other assays. This invention provides the most rapid means currently available for isolating proteins from prokaryotic and eukaryotic total cells. The protein extraction procedures have a dynamic volume ranging from 20-500 µl. The unique features provided by this invention are especially useful in samples where cells available for protein extraction are limiting factors.

The term "polypeptide" refers broadly to a polymer of two or more amino acids joined together by peptide bonds. The term "polypeptide" also includes molecules which contain more than one polypeptide joined by disulfide bonds, ionic bonds, or hydrophobic interactions, or complexes of polypeptides that are joined together, covalently or noncovalently, as multimers (e.g., dimers, tetramers). Thus, the terms peptide, oligopeptide, and protein are all included within the definition of polypeptide and these terms are used interchangeably.

"Isolated" polypeptides refer to polypeptides that have been removed from their natural environment.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. Drawing depicting an embodiment of a spin column with a hydrophobic porous filter (black area, 3) installed in accordance with the invention.

FIG. 2. Drawing depicting an embodiment of a collection tube having an optional hinged sealing cap 5.

FIG. 3. Drawing depicting an embodiment of the invention in which the spin column with hydrophobic filter medium 3 is placed inside a collection tube 6.

DETAILED DESCRIPTION OF ILLUSTRATIVE EMBODIMENTS

Figure 4:
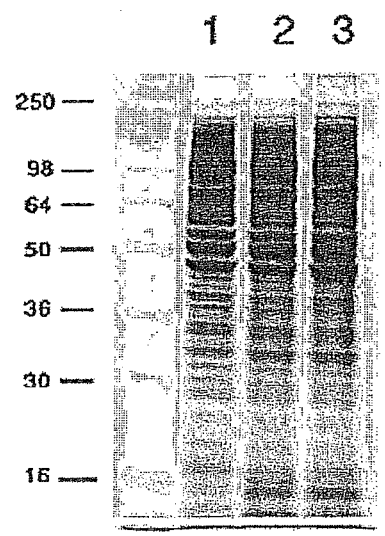
FIG. 4. Coomassie blue stained SDS-PAGE using denaturing cell lysis buffer to extract proteins from mouse cells.

This invention provides methods, reagents, and apparatus for rapidly extracting proteins from eukaryotic and prokaryotic cells. Examples of eukaryotic cells include, for instance, vertebrate cells including murine cells such as mouse and rat, human cells, and any other mammalian animal cell. Prokaryotic cells include, for instance, single celled bacteria and archaea. One aspect of the invention features a centrifuge/vacuum column apparatus (e.g. spin column device) for extracting proteins from mammalian and/or bacterial cells. The apparatus includes a chamber 2 with a hydrophobic filtering medium 3 with defined pore size (FIG. 1) and a collection tube 6 with an optional hinged cap 5 (FIG. 2). This apparatus is referred to as protein extraction filter cartridge 7 (FIG. 3). The cells are first lysed by cell lysis buffers and the viscous cell lysate (due to the release of genomic DNA) is transferred to the chamber 2 of a protein extraction cartridge using, for instance, a pipetting device. Upon subjecting the apparatus to centrifugation the cell lysate passes through the filtering medium 3 and through the smaller opening 4 into the collection tube 6 (FIG. 2). As a result, majority of genomic DNA and cell/tissue debris is retained on the filter medium 3, and the proteins pass through the filter medium 3 and are present at the bottom of the collection tube 6.

The invention further provides reagents for use with the apparatus of the invention to minimize the extraction time and to maximize protein yield. Reagents have been developed for 1) extracting denataured total proteins from mammalian cells and tissues, 2) extracting native total proteins from mammalian cells and tissues, 3) separating mammalian cells and tissue proteins into cytoplasmic and nuclear compartments, and 4) extracting denatured total proteins from bacterial cells. Proteins extracted by the apparatus and reagents are suitable for use in applications including SDS-PADE, 2-dimensional gel analysis, immunoblotting, ELISA, gel mobility shift assay, immunoprecipitation and other assays. An apparatus of this invention can also be coupled with other buffer systems for extracting proteins from insect, yeast and plant cells.

The present invention provides many advantages over the prior art in terms of speed, neatness, consistency, and protein yield. Most current protein extraction procedures are tedious and time-consuming. Many commercial protein extraction procedures require more than 30 minutes to complete. With present invention, in one embodiment, such as protein extraction under denaturing conditions, can be accomplished in less than five minutes, less than four minutes, less than three minutes, less than two minutes, or less than one minute. In one embodiment, such as protein extraction under native conditions, protein extraction can be accomplished in less than eight minutes, less than seven minutes, less than six minutes, less than five minutes, less than four minutes, less than three minutes, less than two minutes, or less than one minute. In one embodiment, such as protein extraction of cytoplasmic and nuclear proteins, protein extraction can be accomplished in less than 15 minutes, less than 14 minutes, less than 13 minutes, less than 12 minutes, less than eleven minutes, less than ten minutes, less than nine minutes, or less than eight minutes. In one embodiment, such as protein extraction from bacterial cells, protein extraction can be accomplished in less than five minutes, less than four minutes, less than three minutes, less than two minutes, or less than one minute. A preferred embodiment of this invention is to lyse the cell with lysis buffer, transfer the viscous cell lysate to chamber 2 and subject to 30 seconds centrifugation in a microcentrifuge. The non-viscous protein extract present in the collection tube 6 is ready for subsequent analysis and down steam downstream applications. Due to the use of protein extraction filter cartridge, buffers, pre-defined lysate volume, and pre-defined centrifugal force, the quality of extracted proteins is consistent with high yield. This invention is especially useful when the available cell number is a limiting factor. With the present invention, protein extraction procedure can be accomplished in as short as 1 minute. Total proteins can be extracted from cell numbers as few as $3 \times 10^5$ with an extraction volume as small as 20 µl, which ensures satisfactory protein concentration for downstream applications. The use of protease to prevent protein degradation is a common practice for many commercial protein extraction kits however with the present invention the use of protease is not necessary because of the significantly shortened extraction time.

A. The Protein Extraction Filter Cartridge

The present invention is best understood with the aid of the accompanying Figures. Referring to FIG. 1, the invention provides a protein extraction apparatus comprising a spin column having a chamber 2 with a larger opening 1 and a smaller opening 4 having porous filtering medium 3 inserted for extracting proteins and retaining genomic DNA. The average pore size of the filtering medium used in this invention is 30 µm however a pore size of 10, 20, 40, 50, and 60 µm does not adversely affect protein recovery. The thickness of the filter medium may vary. One preferred embodiment is to use a filter medium thickness of 6 mm which provides retention of genomic material and a satisfactory volume of extracted proteins. The thickness of the filter medium can be in a range of 0.5-20 mm in a spin column format, such as 0.5, 1, 2, 4, 6, 8, 10, 15, 18, and 20 mm. Examples of hydrophobic materials that can be used include, but are not limited to, polyethylene glycol, polyvinylidene fluoride, etc. Though hydrophobic plastic filtering medium is the preferred material used in present invention, in some embodiments hydrophilic materials or hydrophilic materials with hydrophobic coatings may also be used. In addition to materials mentioned above, it may be possible to use other materials such as porcelain, rubber, and silicon filters. To extract proteins using the apparatus, the spin column with filtering medium 3 is placed in a collection tube 6 (FIG. 2) having an optional hinged cap 5 to form a complete protein extraction filter cartridge 7 (FIG. 3). To extract proteins from biological samples, the cells and tissues are lysed with an appropriate buffer solution, transferred to the protein extraction cartridge and centrifuged in a microcentrifuge for 30 seconds at 12,000-16,000 rpm at room temperature or at 4° C. Lysate passing through the filter medium 3 is collected in the collection tube 6 that contains extracted proteins.

B. Protein Extraction Solutions

A feature of the invention is the use of a buffer system for a variety of protein extraction applications. The buffer system coupled with protein extraction filter cartridge (s) can be used to extract either native or denatured proteins from biological samples. The apparatus can also be used for protein fractionations of mammalian cells and tissues.

(1) Solution A (Denaturing Cell Lysis Buffer)

Solution A is used for extraction of denatured total proteins from eukaryotic cells and tissues. It includes one or more surfactants and/or detergents, and a metal chelator in a buffered solution. One surfactant may be an anionic surfactant, such as sodium dodecyl sulfate (SDS). The concentration of SDS may be between 0.01% (wt/vol) and 5.0% (wt/vol), including, for instance, 0.01%, 0.05%, 0.1%, 0.15%, 0.2%, 0.25%, 0.3%, 0.35%, 0.4%, 0.45%, 0.5%, 0.8%, 1.0%, and 5.0%. Optionally and preferably, the solution includes a second surfactant or detergent, including, but not limited to, polyethylene glycol p-(1,1,3,3-tetramethylbutyl)-phenyl ether (available under the trade name Triton X-100), octylphenoxypolyethoxyethanol (available under the trade name Nonidet P-40), polyoxyethylene (20) sorbitan monolaurate (available under the trade name Tween-20), or digitonin. The second surfactant and/or detergent in the buffer effectively prevents SDS from precipitating at 4° C. The concentration of the second surfactant and/or detergent may be between 0.05% (vol/vol) and 2.0% (vol/vol), including, for instance, 0.05%, 0.1%, 0.2%, 0.4%, 0.8%, 1.0%, and 2.0%. A useful metal chelator includes, but is not limited to, ethyenediamineletracetate (EDTA). The metal chelator may be at a concentration between 0.1 mM and 10 mM, such as 5 mM. The solution may be buffered using any buffering system, such as phosphate-buffered saline (PBS), at a pH of between 6.5 and 8.0, such as 7.5. An example of a PBS solution is 0.2 grams KCl, 0.2 grams $KH_2PO_4$, 8 grams NaCl, and 2.16 grams $Na_2HPO4*7H_2O$ in 1000 ml $H_2O$. Other components may be added, such as 0.1-2.0% of sodium deoxycholate, provided the additional components do not adversely affect the buffer efficacy. The presence of 0.1×PBS in the buffer is for maintaining appropriate pH, and it can be replaced with 1×PBS and other buffers as long as the pH of the solution is maintained in the range of 6.5 to 8.0. Solution A may be used with cells that are present in a pellet having a volume of between 10 µl and 30 µl, such as 20 µl. In one embodiment, a solution for use in the extraction of denatured total proteins from eukaryotic cells and tissues does not include chaotropic agents, such as urea, thiourea, lithium perchlorate, or guanidinium compounds such as guanidinium thiocyanate, guanidinium isothiocyanate, and guanidinium chloride.

(2) Solution B (Native Cell Lysis Buffer)

Solution B is used for extraction of native total proteins from eukaryotic cells and tissues. It includes one or more surfactants and/or detergents, a metal chelator, and a salt in a buffered solution. An example of a surfactant and/or detergent includes, but is not limited to, Triton X-100. The surfactant and/or detergent may be between 0.05% (vol/vol) and 2.0% (vol/vol), including, for instance, 0.05%, 0.1%, 0.2%, 0.4%, 0.8%, 1.0%, and 2.0%. A useful metal chelator includes, but is not limited to, ethyenediamineletracetate (EDTA). The metal chelator may be at a concentration between 0.1 mM and 10 mM, such as 5 mM. A useful salt includes, but is not limited to, sodium chloride (NaCl), and may be between 200 mM and 500 mM, including, for instance, 200, 300, 400 and 500 mM. The solution may be buffered using any buffering system, such as phosphate-buffered saline (PBS), at a pH of between 6.5 and 8.0, such as 7.5. Solution B may be used with cells that are present in a pellet having a volume of between 10 µl and 30 µl, such as 20 µl.

(3) Solution C (Cytoplamic Extraction Buffer)

Solution C is used for extracting the cytoplasmic fraction from eukaryotic cells and tissues. It includes one or more surfactants and/or detergents and a metal chelator in a buffered solution. The surfactant and/or detergent may be Nonidet P-40 (NP-40). The surfactant and/or detergent may be between 0.02% (vol/vol) and 1.0% (vol/vol), including, for instance, 0.2%, 0.4%, 0.8%, and 1.0%. A useful metal chelator includes, but is not limited to, ethyenediaminel-etracetate (EDTA). The metal chelator may be at a concentration between 0.1 mM and 10 mM, such as 5 mM. The solution may be buffered using, for instance, Tris-(hydroxymethyl)aminomethane (Tis-HCl). The concentration of the buffer may be between 1 mM and 100 mM, such as 10 mM. The pH may be between 6.0 and 9.0, such as 8.0. The surfactant and/or detergent, such as NP-40, is chosen for disrupting cell membranes to release cytosol proteins without significant effect on nuclear membranes. The concentration of NP-40 ranging from 0.02-1.0% can be used depending upon cell types involved. Solution C can be substituted with other buffer solutions such as, for instance, 10 mM HEPES buffer, pH 7.5 or 0.1×PBS, pH 7.4. Solution A may be used with cells that are present in a pellet having a volume of between 10 µl and 30 µl, such as 20 µl.

(4) Solution D (Bacterial Cell Lysis Buffer)

Solution D includes surfactants and/or detergents, a hydroxide, and a metal chelator in a buffered solution. One surfactant is SDS. The concentration of SDS may be between 0.1% (wt/vol) and 2.0% (wt/vol), including, for instance, 0.1%, 0.2%, 0.4%, 0.6%, 0.8%, 1.0%, and 2.0%. The solution includes a second surfactant or detergent, such as, but not limited to, Triton X-100. The second surfactant and/or detergent in the buffer may aid in minimizing protein aggregation after alkaline lysis and subsequent neutralization. The concentration of the second surfactant and/or detergent may be between 0.05% (vol/vol) and 2.0% (vol/vol), including, for instance, 0.05%, 0.1%, 0.2%, 0.4%, 0.8%, 1.0%, and 2.0%. The hydroxide, such as sodium hydroxide or potassium hydroxide, is present at a concentration of between 0.05 N and 0.5 N, such as 0.1 N NaOH. A useful metal chelator includes, but is not limited to, EDTA. The metal chelator may be at a concentration between 1 mM and 20 mM, such as 5 mM. The solution may be buffered using any buffering system at a pH of between 10.0 and 12.0, such as PBS, 20 mM Tris-HCl, or 20 mM HEPES buffers.

(5) Solution E

Solution E includes a compound suitable for for neutralization of solution D to a pH of approximately 8.0. For instance, hydrochloride (HCl) at a concentration of between 0.5 N to 1.5 N, such as 0.5 N, 0.7 N, 0.9 N, 1.1 N, 1.3 N, or 1.5 N may be used. In another embodiment, 2-[4-(2-hydroxyethyl)piperazin-1-yl]ethanesulfonic acid (HEPES) at a concentration of between 0.8 M and 1.6 M, such as 0.8 M, 1.0 M, 1.2 M, 1.4 M, or 1.6 may be used. The concentration of solution E can be adjusted according to NaOH concentration used in solution D.

The present invention is illustrated by the following examples. It is to be understood that the particular examples, materials, amounts, and procedures are to be interpreted broadly in accordance with the scope and spirit of the invention as set forth herein.

Example 1

Extraction of Denatured Total Proteins from Mammalian Cells

Prior to protein extraction, the protein extraction filter cartridge with collection tube was pre-chilled on ice. The cells were harvested by low speed centrifugation and washed once with cold PBS. After transfer of the cells to a 1.5 ml microcentrifuge tube they were pelleted by centrifugation at 3000 rpm for 2-3 min. The supernatant was completely aspirated. Two hundred microliters of solution A were added to 20 µl packed cell volume and the pellet resuspended by pipetting up and down a few times to lyse the cells. The cell lysate was transferred to pre-chilled filter cartridge(s), the tube capped and centrifuged in a table-top microcentrifuge for 30 seconds at 12,000-16,000 rpm at 4° C.

The collection tube was immediately placed on ice and the filter cartridge discarded. The cell lysate was now ready for downstream applications. The protein yield with this protocol was about 2.0-2.8 mg/ml depending upon the cell types. FIG. 4 (SDS-PAGE) shows a comparison of proteins extracted by repeated sonication and proteins extracted by solution A coupled with protein extraction cartridge of present invention. Lane 1, proteins prepared by repeated sonication; Lanes 2 and 3, proteins extracted by solution A.

Example 2

Extraction of Native Total Proteins from Mammalian Cells

Figure 5:
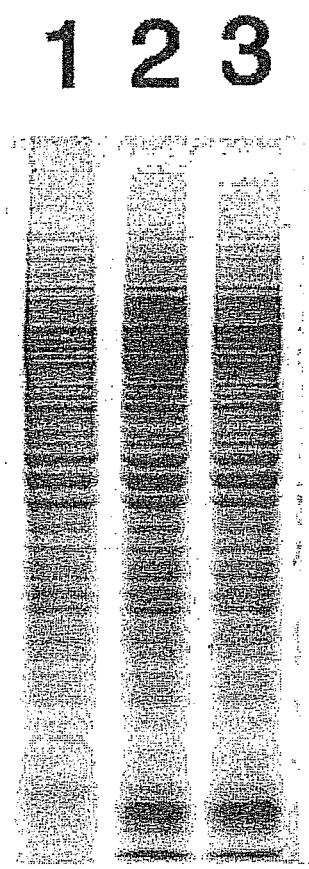
FIG. 5. Coomassie blue stained SDS-PAGE using native cell lysis buffer to extract proteins from human kidney epithelium cell (293T).

The cells were prepared for protein extraction as described in Example 1. After washing the cell pellet (20 µl packed cell volume) with PBS, 200 µl solution B was added to the cell pellet and vortexed vigorously for 15 seconds. The tube was placed in ice for one minute, and the procedure was repeated four times. The cell lysate was transferred to a pre-chilled filter cartridge, the tube was capped and centrifuged in a table-top microcentrifuge for 30 seconds at 12,000-16,000 rpm at 4° C. The collection tube was immediately placed on ice and the filter cartridge was discarded. The protein yield with this protocol was about 2.0-2.8 mg/ml depending upon the cell types used. FIG. 5 (SDS-PAGE) shows a comparison of proteins extracted with solution A and those with solution B of present invention. Lane 1, 293T cell proteins extracted by solution A. Lane 2 and 3, proteins extracted by solution B.

Example 3

Extraction of Cytoplamic and Nuclear Proteins from Mammalian Cells

Figure 6:
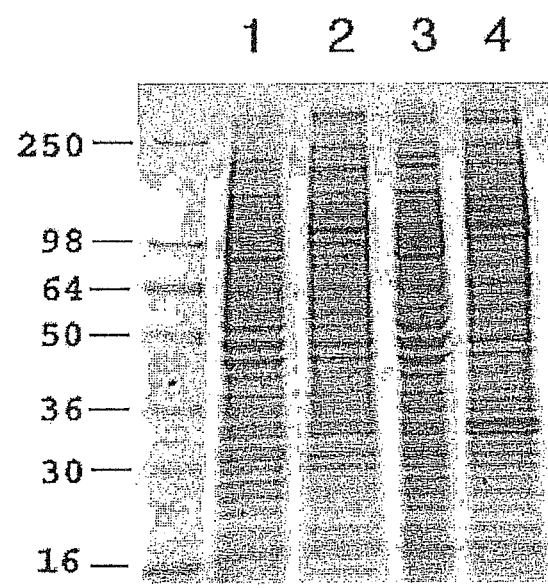
FIG. 6. Coomassie blue stained SDS-PAGE using cytolasmic and nuclear extraction buffers to extract proteins from 293T cells.

Cell preparation for protein fractionation is the same as in Example 1. After washing 20 µl packed 293T cells with PBS, the cells were resuspended in 200 µl solution C, the tube vortexed vigorously for 15 seconds and the tube incubated on ice for 5 minutes. The tube was centrifuged for 5 minutes at top speed in a microcentrifuge at 4° C. The supernatant (cytosol fraction) was transferred to a fresh pre-chilled 1.5 ml tube. One hundred microliters buffer B was added to the pellet, vortexed vigorously for 15 seconds, and the tube incubated on ice. The 15 second vortexing and one minute incubation steps were repeated 4 times. The cell lysate was immediately transferred to a pre-chilled filter cartridge and centrifuged at 12,000 to 16,000 rpm in a microcentrifuge at 4° C. for 30 seconds. The collection tube (containing nuclear extract) was immediately placed on ice and the filter cartridge discarded. The proteins may be stored at −80° C. until use. FIG. 6 (SGS-PAGE) shows a comparison of protein extraction results of the invention with a commercially available kit (lanes 1 and 2) with the method of Example 3 (lanes 3 and 4). Lane 1, Cytoplasmic fraction (commercially available kit), Lane 2, nuclear fraction (commercially available kit). Lane 3, Cytoplasmic fraction (method of Example 3), Lane 4, nuclear fraction (method of Example 3).

Example 4

Extraction of Denatured Total Proteins from Bacterial Cells

Figure 7:
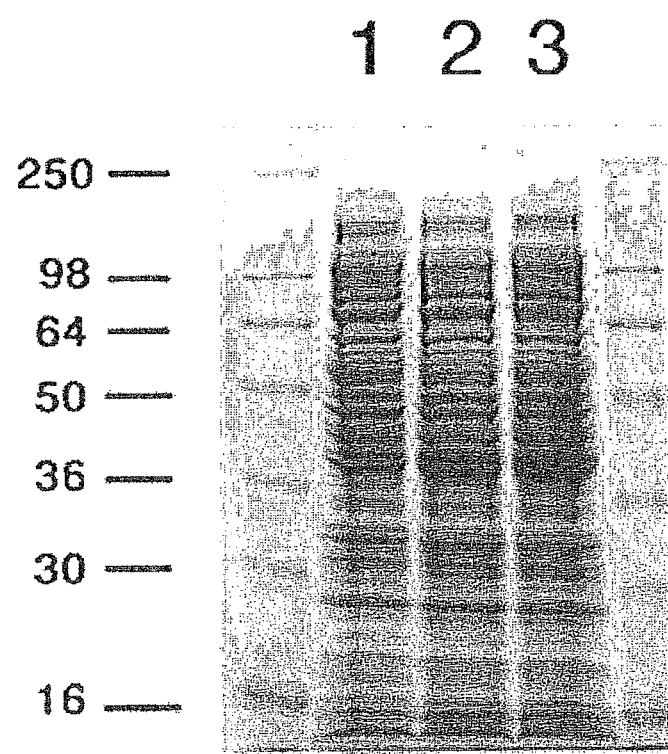
FIG. 7. Coomassie blue stained SDS-PAGE using the bacterial cell lysis buffers to extract proteins from *E. coli*.

Prior to protein extraction the protein extraction filter cartridge with collection tube were pre-chilled on ice. The cell in the bacterial culture were pelleted in a 1.5-2.0 ml microcentrifuge tube in a table-top microcentrifuge at top speed for 1-2 min. The supernatant was removed and the cell pellets washed in cold PBS once. The supernatant were aspirated completely. Two hundred microliters of solution D were added to the cell pellet and the pellet resuspended by pipetting up and down a few times to lyse the cells. Twenty microliters of solution E were added to the lysate and vortexed vigorously for 15 seconds. The cell lysate was transferred to a pre-chilled filter cartridge, the tube capped and centrifuged in a table-top microcentrifuge for 30 seconds at 12,000-16,000 rpm at 4° C. The collection tube was immediately placed on ice and the filter cartridge discarded. The cell lysate was now ready for downstream applications. The protein yield was about 1.5-1.8 mg/ml. FIG. 7 (SDS-PAGE) shows a comparison of bacterial proteins extracted by repeated sonication and those with present invention. Lane 1, represents total proteins isolated from *E. coli* by repeated sonication. Lane 2 and 3 represent two separated experiments of isolating proteins from *E. coli* with present invention.

Example 5

Comparison of Methods Described Herein with Commercially Available Methods

There are several isolation kits in the market for the extraction of protein followed by nucleic acids, which may appear similar to the methods presented herein; however a closer look at the commercially available isolation kits reveals significant differences. According to the manufacturers, isolation kits employ a spin column format and can sequentially extract DNA, RNA and protein from a single sample. The commercially available kits may use a nucleic acid binding resin or be membrane based. The sample is lysed with cell lysis buffer, the cell lysate transferred to the spin column, and then centrifuged. DNA and RNA are bound to the matrix, and the flow through contains proteins. After centrifugation, the spin column is sequentially washed with washing buffer and DNA/RNA is eluted from the column with elution buffer.

Commercially available kits are designed to extract DNA/RNA/proteins sequentially. In order to inactivate nucleases (DNAses or RNAses), the cell lysis buffers contains a high concentration of chaotropic agents such as guanidinum thiocyanate and/or guanidium isothocyanate as well as other salts for nucleic acids to bind to the matrix. These chaotropic agents are strong denaturants and may cause protein degradation. In order to bind RNA to matrix alcohol must be added to cell lysis buffer that may precipitate some proteins in the cell lysate. Due to the presence of strong denaturants in the lysis buffer, it can be much more difficult, and is often not possible, to extract native proteins with commercially available kits. The buffer system in commercially available kits is not compatible with protein extraction from bacterial samples. In order for nucleic acids to bind to the matrix efficiently, diluted cell lysate must be used in commercially available kits (<33 $10^6$) therefore the protein concentration in the flow through is very low (100-200 µg/ml). In fact, due to the presence of high salt and chaotropic agents in the cell lysis buffers of commercially available kits, it is often recommended by manufacturers that proteins in flow through be precipitated/concentrated prior to use.

Major differences between the methods described herein and commercially available kits are summarized below:

|  | Methods described herein | commercially available kits |
|---|---|---|
| Spin column matrix | Thick porous filter | Thin membrane/resin |
| Mechanism of action | Retain/shear DNA | Bound DNA/RNA |
| Lysis buffer | Protein friendly | Chaotropic agent |
| Extracted protein concentration | 2-4 mg/ml | 100-200 ug/ml |
| Protein representation | Full representation | Partial representation |
| Extract Native proteins | Yes | No |
| Extract bacterial proteins | Yes | No |
| Protein band patterns in SDS-PAGE | Normal | Altered |

Figure 8A:
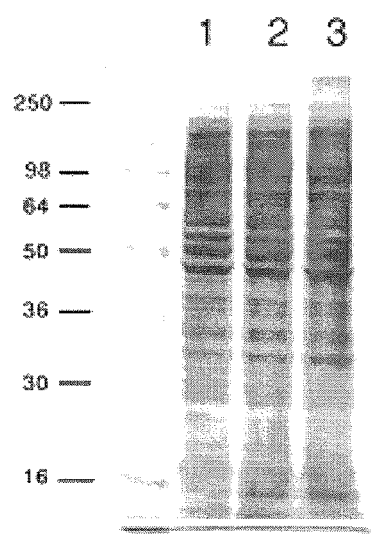
FIG. 8. A. Coomassie blue stained 12% SDS-PAGE. B. Western blotting. Proteins separated in 12% SDS-PAGE (shown in FIG. 8A) were transferred to nitrocellulose membrane and probed with anti-mouse MDM2, HDAC1 and actin. Lane 1, NIH 3T3 cell lysate prepared by repeated sonication; lanes 2 and 3, proteins isolated using denaturing cell lysis buffer described herein.
Figure 8B:
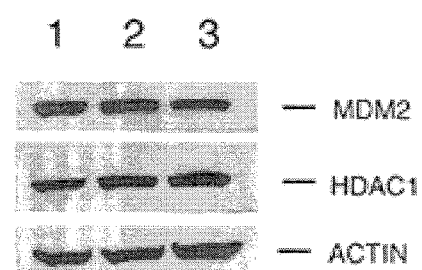
Figure 9:
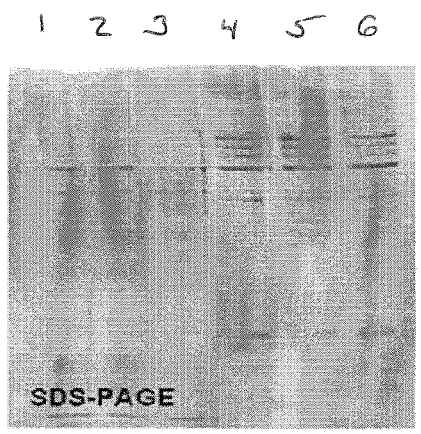
FIG. 9. Left panel, coomassie blue stained 12% SDS-PAGE of proteins isolated using commercially available kits. Lanes 1, 2, and 3, commercially available kit A; lanes 4, 5, and 6, commercially available kit B.

Comparison of protein band patterns of mammalian cells using the methods described herein and a commercially available kit. Comparison of FIG. 8 with FIG. 9 shows use of the commercially available kits results in only partial representation of the proteins and an alteration of the protein bands. Commercially available kits do not use a porous filter to isolate proteins from total cell lysates and they do not provide the desired recovery, speed and ease of separation offered by this invention.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for isolating polypeptides from cells comprising:
    contacting cells with a lysis buffer, wherein cell lysis occurs resulting in a viscous cell lysate, and wherein the cell lysis buffer comprises a surfactant, a detergent, or a combination thereof, and a metal chelator;
    passing the viscous cell lysate through a porous filtering medium, wherein genomic DNA and debris are retained by the porous filtering medium and polypeptides present in the cell lysate pass through the porous filtering medium, and wherein the porous filtering medium comprises a pore size of at least 10 to no greater than 60 microns and a thickness of at least 0.5 millimeter to no greater than 20 millimeters; and
    collecting the filtrate, wherein the filtrate comprises a non-viscous polypeptide extract comprising isolated polypeptides, wherein the isolated polypeptides comprise the polypeptides present in the cell lysate.

2. The method of claim 1 wherein the lysis buffer comprises a detergent.

3. The method of claim 2 wherein the detergent is selected from SDS, Triton X-100, Nonidet P-40, Tween-20, and digitonin.

4. The method of claim 1 wherein the lysis buffer comprises more than one detergent.

5. The method of claim 1 wherein the lysis buffer does not comprise a chaotropic agent.

6. The method of claim 1 wherein the lysis buffer is buffered at a pH of between 7.0 and 12.

7. The method of claim 1 wherein the filter medium is hydrophobic.

8. The method of claim 1 wherein the filter medium is hydrophilic.

9. The method of claim 1 wherein the cells are vertebrate cells.

10. The method of claim 9 wherein the vertebrate cells are cultured cells.

11. The method of claim 9 wherein the vertebrate cells are present in a tissue.

12. The method of claim 1 wherein the contacting comprises contacting cells that are present in a volume of at least 20 μl.

13. The method of claim 1 wherein the contacting comprises contacting cells that are present in a volume of 20 μl.

14. The method of claim 1 wherein the cells are prokaryotic cells.

15. The method of claim 1 wherein the passing comprises centrifugation, and the centrifugation occurs for 30 seconds.

* * * * *